United States Patent [19]

Wolfla, II

[11] 3,995,491
[45] Dec. 7, 1976

[54] ERGOMETER

[75] Inventor: Lyman H. Wolfla, II, Indianapolis, Ind.

[73] Assignee: Preventive Cardiopath Systems, Inc., Indianapolis, Ind.

[22] Filed: Aug. 18, 1975

[21] Appl. No.: 605,719

[52] U.S. Cl. .................................. 73/379; 272/73
[51] Int. Cl.² .......................................... G01L 5/02
[58] Field of Search ............... 73/379, 519; 272/73; 324/174

[56] References Cited
UNITED STATES PATENTS

| | | | |
|---|---|---|---|
| 3,767,195 | 10/1973 | Dimick | 73/379 X |
| 3,826,985 | 7/1974 | Wiley | 324/174 X |

Primary Examiner—Jerry W. Myracle
Attorney, Agent, or Firm—Woodard, Weikart, Emhardt & Naughton

[57] ABSTRACT

An ergometer apparatus such as a bicycle-type exerciser including a flywheel driven by a drive sprocket and chain. The flywheel includes a pair of permanent magnets moving past a pickup coil mounted on the frame of the ergometer as the flywheel is rotated. A portion of the voltage from the coil is taken from a potentiometer wiper arm positioned through the tension setting for the load on the flywheel and coupled to a meter calibrated to indicate the work expended by the operator of the ergometer. No external electrical power need be supplied to the metering apparatus.

18 Claims, 6 Drawing Figures

ERGOMETER

BACKGROUND OF THE INVENTION

This invention is in the field of bicycle exercisers.

Bicycle exercisers or ergometers have been used for some time in both athletic and medical-therapeutic applications. While those utilized primarily for exercise purposes, such as at a health club, need only provide an indication of speed of rotation of the flywheel of the ergometer, perhaps with the addition of an odometer, those exercise devices utilized for medical-therapeutic purposes require more precise determination of the power supplied by the patient using the ergometer.

There have been proposed various electrical and mechanical means for determining the speed of rotation of the flywheel of ergometer, as well as the amount of power delivered by the user. Often these speed determining devices are a part of a larger more complicated, system, such as for automatic loading of the flywheel. In all cases, these devices for indicating work have been relatively complex and generally expensive. Mechanical approaches to determining the power supplied by a person using an ergometer are subject to various mechanical difficulties such as breakdowns and need for replacement of worn parts. Externally-powered indicators include those shown in U.S. Pat. No. 2,784,591 to Shoor; U.S. Pat. No. 3,057,201 to Jaeger; U.S. Pat. No. 3,505,992 also to Jaeger; and U.S. Pat. No. 3,715,721 to Lulay et al. Some of these devices, and several others known in the art, utilize magnets and similar structures associated with the flywheel for providing the load on the flywheel rather than using the more standard belt-type load. However, such utilization of magnets is not relevant to the use of magnets for flywheel speed determination.

Previous mechanical methods for work determination have generally been less expensive than the purely electrical methods but are not as reliable. Further, among the electrical methods, none have been provided which are selfpowered. The most relevant prior art patent of which applicant is aware is U.S. Pat. No. 3,767,195 to Dimick, which shows the use of a tachometer pickup including a magnet mounted on the flywheel activating a reed switch. Dimick, however, deals exclusively with an externally powered system and fails to apprehend the use of a pickup coil as set forth herein.

SUMMARY OF THE INVENTION

One embodiment of the invention is, in an exercise apparatus having a frame, a rotatable flywheel member mounted on the frame, pedal means for rotating the flywheel member, and resistance means for opposing the rotation of the flywheel member, the improvement which comprises a permanent magnet mounted on the flywheel member not adjacent its axis of rotation, a pickup means, coupled to the frame and positioned adjacent the path of said magnet as the flywheel member is rotated, producing at an output an amount of electrical energy dependent upon the speed of rotation of the magnet and a meter means coupled to the output of the pickup means for providing an indication of the amount of said electrical energy.

It is an object of the present invention to provide a self-powered electrical indicating apparatus for an ergometer.

It is a further object of the present invention to provide a self-powered electrical work indicating apparatus for an ergometer.

It is a still further object of the present invention to provide such a work indicating apparatus which includes means for varying the electrical indication dependent upon the loading of the flywheel of the ergometer.

Further objects and advantages of the present invention shall be apparent from the following detailed description and accompanying figures.

DESCRIPTION OF THE PREFERRED EMBODIMENT

Figure 1:
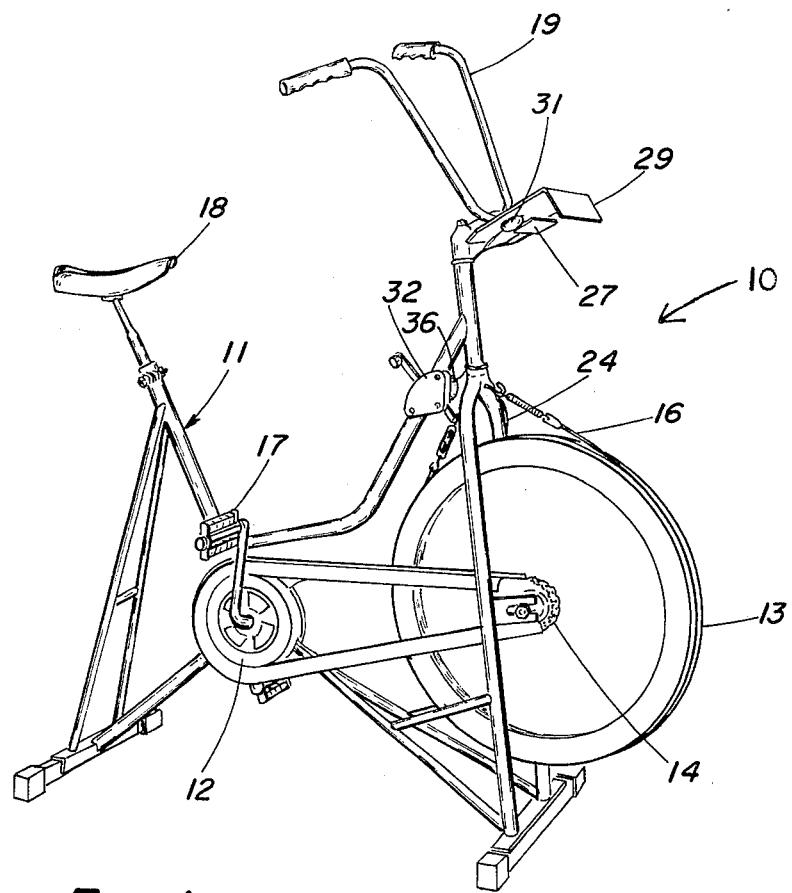
FIG. 1 is a perspective view of an ergometer according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 1 there is shown an ergometer or bicycle exerciser 10 having a frame 11, drive sprocket 12, flywheel 13, chain 14, belt 16, pedals 17, seat 18, and handle bars 19. The flywheel 13 includes a driven sprocket portion receiving chain 14 with the driving force applied to pedals 17 being coupled through chain 14. Flywheel 13 is typically an aluminum material, and the belt 16 is nylon.

Figure 2:
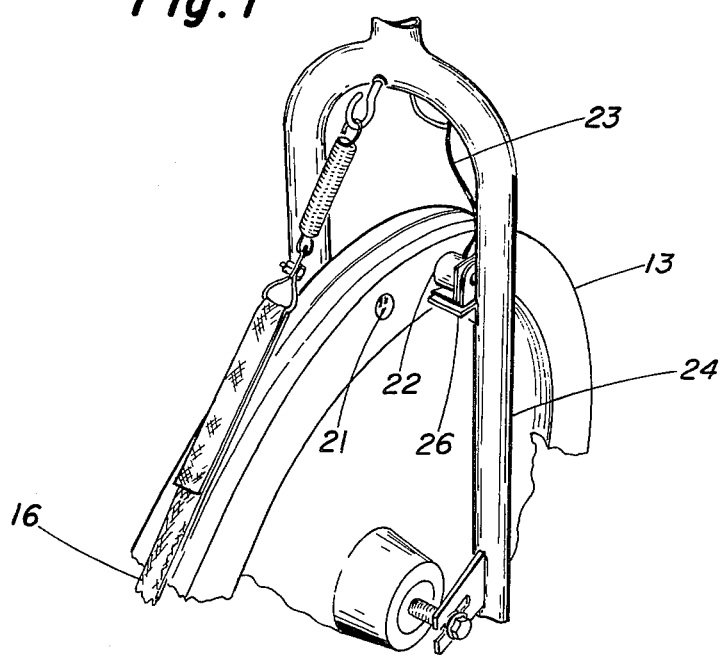
FIG. 2 is an enlarged view of a portion of the front frame section and a portion of the flywheel and belt of the embodiment of FIG. 1, showing a magnet in the flywheel and a pickup coil.
Figure 5:
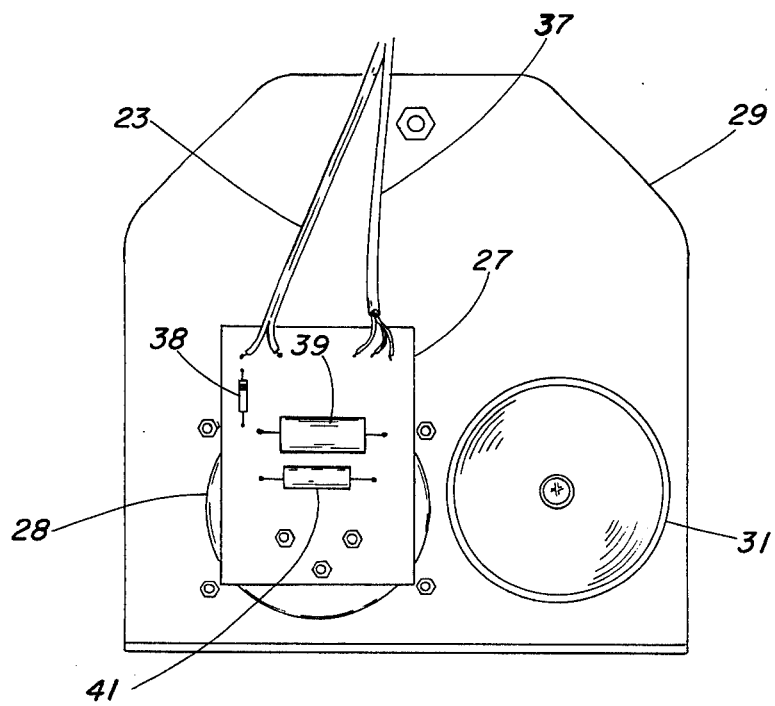
FIG. 5 is a view of the bottom of the work indicator panel shown in FIG. 4.

Referring now to FIG. 2, on the inside of left front fork 24 is mounted a DC coil on a suitable mounting bracket 26. A pair of diametrically opposed permanent magnets such as 21 are emplaced within flywheel 13 as shown. As flywheel 13 is rotated, through the force applied to pedals 17, magnets 21 move past coil 22, setting up a transient magnetic field, inducing a voltage in coil 22. The velocity of rotation of flywheel 13 affects the frequency and duration of the voltage pulses induced in coil 22. Two voltage wave forms are produced by the two magnets for each revolution of flywheel 13. The voltage across coil 22 is coupled by a pair of wires in cable 23 to the circuit board 27 (FIGS. 1 and 5), to be described infra.

Figure 4:
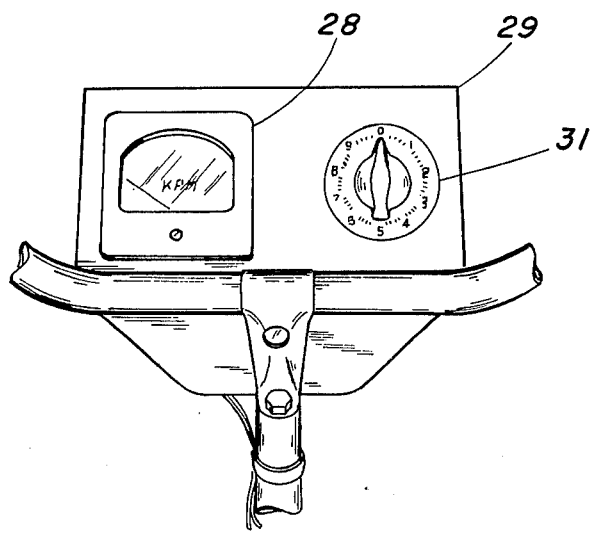
FIG. 4 is an enlarged top view of a portion of the front of the embodiment of FIG. 1 showing the work indicator.

The voltage wave form produced across coil 22 is processed by circuitry on circuit board 27 and a resultant signal is detected by meter 28. Meter 28 (FIGS. 1, 4 and 5) and circuit board 27 are mounted on bracket 29, which is attached to handle bars 19 in conventional manner as shown most precisely in FIGS. 1 and 4. Also provided on bracket 29 is a conventional timer mechanism 31.

Figure 3:
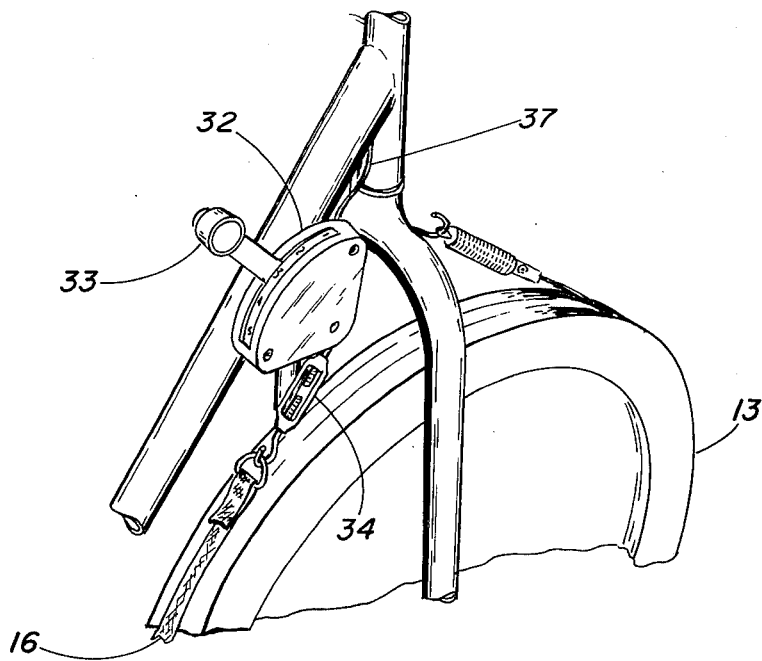
FIG. 3 is an enlarged perspective view of a portion of the flywheel and front frame of the embodiment of FIG. 1 which includes the load adjustment apparatus.

As shown in FIGS. 1 and 3, there is provided for belt 16 a tension-adjust control shown generally at 32. This control adjusts the tension of belt 16 which therefore varies the frictional load on flywheel 13 which must be overcome by the force applied to pedals 17 by the user of the ergometer. As can be best seen in FIG. 3, a lever 33 is pivotally mounted within control casing 32 and may be moved to one of five detented positions. As can be seen, moving lever 33 to position 5 applies the maximum tension to belt 16 as connecting member 34 is moved generally upwardly in reference to the showing of FIG. 3.

As shown in FIG. 1, a potentiometer 36 is mounted to casing 32 and has a wiper arm whose position is determined by the setting of lever 33. The movement of the wiper arm 43 of potentiometer 36 is ganged with the movement of lever 33 in conventional manner, and this relationship is shown diagrammatically in FIG. 6. A three-wire cable for the wiper arm and each end of the resistive element of the potentiometer 37 (FIGS. 3 and 5) is coupled from potentiometer 36 to circuit board 27 on the bottom of bracket 29.

Figure 6:
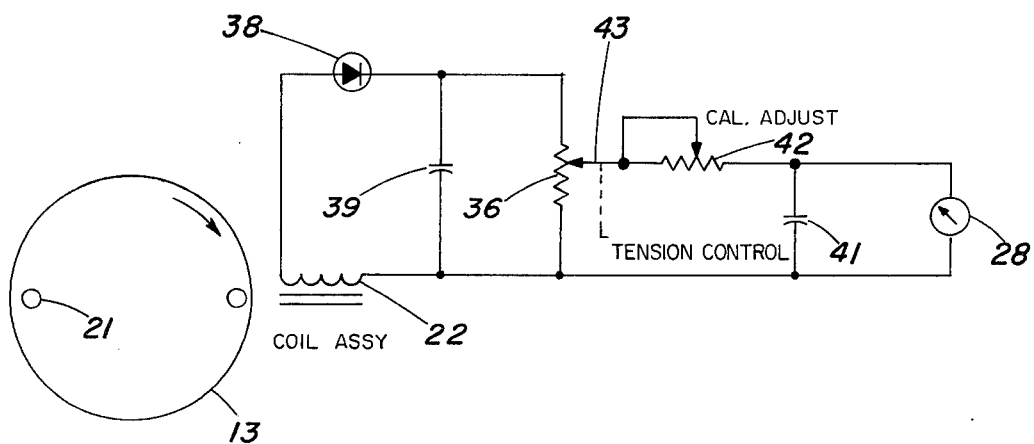
FIG. 6 is a schematic view of the work indicator of the embodiment of FIG. 1.

Referring now to FIG. 6, there is shown diagrammatically the circuitry for providing an indication of the power delivered by a user of exerciser 10. As flywheel 13 rotates, magnets 21 move past, and establish voltage pulses in, coil 22. Diode 38 and capacitor 39 half-wave rectify the pulses produced across coil 22. The resistive element of potentiometer 36 is connected across capacitor 39 through two of the wires in cable 37. Through the other lead in cable 37, a portion of the voltage is picked off the resistive element by wiper arm 43 of potentiometer 36 and coupled to a calibration adjust potentiometer 42. This potentiometer is mounted on the upper side of circuit board 27 and is adjusted at the same time of assembly and calibration of the ergometer utilizing this power measuring apparatus. The voltage from potentiometers 42 and 43 is applied across ammeter 28 and protection capacitor 41, ammeter 28 functioning essentially as a very sensitive volt meter in this instance.

Typical values for the components of the circuitry of FIG. 6 are 100 microfarads for capacitor 39, 50 microfarads for capacitor 41, 10K ohms for potentiometer 36, and 20K ohms for potentiometer 42. In the presently described embodiment, ammeter 28 is 50 microamperes at full scale. The meter as used in the present embodiment is scaled for a reading of 1200 kilopoundmeters at full scale.

The generally accepted unit of work for an ergometer is the kilopondmeter which is defined as the product of the circumference of the flywheel in meters times the revolutions-per-minute of the flywheel times the force in kilograms of the belt around the flywheel. With reference to FIG. 6, the greater the speed of flywheel 13, the greater the voltage across coil 22 and hence built up on filter capacitor 39. The setting of potentiometer 36 is such that for the lowest tension setting (No. 1) of the tension control, the wiper arm is at its lowest position with reference to FIG. 6. For the highest tension setting of the tension control (No. 5) wiper arm 43 is toward the top of the resistive element of potentiometer 36 as shown in FIG. 6. Therefore, at the higher belt tensions, greater proportions of the voltage across capacitor 39 are coupled to meter 28. Depending upon the circumference of flywheel 13 and the tension applied by belt 16, calibration-adjust potentiometer 42 may be set to obtain, for example, a full scale reading on meter 28 (at a maximum work indication such as 1,200 kilopoundmeters) at the appropriate revolutions per minute of flywheel 13. For calibration purposes, the pulse frequency at the coil 22 may be easily determined and divided by two to determine the speed of rotation of the flywheel.

The use of a DC core coil, such as a relay coil, for coil 22 insures that the core of the coil will not become magnetized. There are no mechanical parts operating at flywheel speeds, eliminating the excessive wear problems of prior art mechanical systems. The sole mechanical contact is the wiper arm contacting the resistive element of potentiometer 36, and since this is not a high-speed wear contact, the potentiometer materials may be selected for long life well within the state of the potentiometer art. The movement of the flywheel 13 itself provides the electrical power to drive the indicator needle of meter 28, and with the modification introduced by potentiometr 36 to reflect the tension setting of belt 16, an indication of the power delivered by the user of the ergometer is provided in a self-powered, maintenance free, electrical system.

While there have been described above the principles of this invention in connection with specific apparatus, it is to be clearly understood that this description is made only by way of example and not as a limitation in the scope of the invention.

What is claimed is:

1. In an exercise apparatus having a frame, a rotatable flywheel member mounted on the frame, pedal means for rotating the flywheel member, and resistance means for opposing the rotation of the flywheel member, the improvement which comprises:
   a permanent magnet mounted on the flywheel member not at its axis of rotation;
   pickup means, coupled to the frame and positioned adjacent the path of said magnet as the flywheel member is rotated, producing at an ouput an amount of electrical energy dependent upon the speed of rotation of the magnet; and
   meter means coupled to the output of the pickup means for providing an indication of the amount of said electrical energy.

2. The apparatus of claim 1 in which the pickup means comprises a coil positioned adjacent the path of the magnet and further comprising circuit means coupled between the coil and the meter means for modifying and rectifying the output of the coil.

3. The apparatus of claim 2 which further comprises control means coupled to the frame for varying the opposition of the resistance means to the rotation of the flywheel member, the setting of the control means affecting the degree of coupling from the output of the pickup means to the meter means.

4. The apparatus of claim 3 in which the circuit means comprises a potentiometer coupled across the rectified output of the pickup means having a wiper arm coupled to the meter means, the position of the wiper arm of the potentiometer being determined by the setting of the control means.

5. The apparatus of claim 4 in which the flywheel member is essentially disc shaped having a generally smooth circumferential surface, and the resistance means comprises a belt biased against a major portion of the circumference of the flywheel, the control means varying the tension of the belt against the flywheel.

6. The apparatus of claim 5 in which the meter means provides an analog indication of the power supplied in rotating the flywheel member for a given opposition of the belt as determined by the setting of the control means.

7. The apparatus of claim 6 in which the pedal means comprises a rotatable drive member mounted on the frame and coupling means for rotating the flywheel member when the drive member is rotated.

8. In an exercise apparatus having a frame, a rotatable drive member mounted on the frame, a rotatable flywheel member mounted on the frame, coupling means for rotating the flywheel member when the drive member is rotated and resistance means for opposing the rotation of the flywheel member, the improvement which comprises:
   a permanent magnet mounted on one of said rotatable members not at its axis of rotation;
   pickup means, coupled to the frame and positioned adjacent the path of said magnet as its associated rotatable member is rotated, for producing at an output an amount of electrical energy dependent upon the speed of rotation of the magnet; and
   meter means coupled to the output of the pickup means for providing an indication of the amount of said electrical energy.

9. The apparatus of claim 8 in which the sole source of energy for the meter means is provided from the output of the pickup means.

10. The apparatus of claim 9 in which the pickup means comprises a coil positioned adjacent the path of the magnet and further comprising circuit means coupled between the coil and the meter means for rectifying and modifying the output of the coil.

11. The apparatus of claim 10 which further comprises control means coupled to the frame for varying the opposition to the rotation of the flywheel member of the resistence means, the setting of the control means affecting the degree of coupling from the output of the pickup means to the meter means.

12. The apparatus of claim 11 in which the meter means provides an analog indication of the power supplied in rotating the flywheel member for a given opposition of the belt as determined by the setting of the control means.

13. The apparatus of claim 12 in which the circuit means comprises a potentiometer coupled across the rectified output of the pickup means having a wiper arm coupled to the meter means, the position of the wiper arm of the potentiometer being determined by the setting of the control means.

14. The apparatus of claim 13 in which the flywheel member is essentially disc shaped having a generally smooth circumferential surface and the resistance means comprises a belt biased against a major portion of the circumference of the flywheel, the control means varying the tension of the belt against the flywheel.

15. The apparatus of claim 14 which further comprises a second magnet mounted on the flywheel member diametrically opposite the first magnet.

16. The apparatus of claim 15 in which the rotatable drive member is a drive sprocket having attached pedals and the coupling means is a chain engaged by the sprocket and also by a sprocket portion on the flywheel.

17. In an exercise apparatus having a frame, a rotatable flywheel member mounted on the frame, pedal means for rotating the flywheel member, and resistance means for opposing the rotation of the flywheel member, the improvement which comprises:
   first means, not coupled to a source of electrical energy, for producing at an output an amount of electrical energy dependent upon the speed of rotation of the flywheel member relative to the frame;
   meter means coupled to the output of the first means for providing an indication of the amount of said electrical energy; and
   control means coupled to the frame for varying the opposition of the resistance means to the rotation of the flywheel member, the setting of the control means affecting the degree of coupling from the output of the first means to the meter means.

18. The apparatus of claim 17 which further comprises a potentiometer coupled across the output of the first means and having a wiper arm coupled to the meter means, the position of the wiper arm of the potentiometer being determined by the setting of the control means.

* * * * *